United States Patent
Duckett, III

(10) Patent No.: US 11,656,450 B2
(45) Date of Patent: May 23, 2023

(54) ROD LENS RELAY SYSTEM WITH REDUCED CHROMATIC ABERRATION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 226 days.

(21) Appl. No.: 17/129,391

(22) Filed: Dec. 21, 2020

(65) Prior Publication Data
US 2022/0197007 A1 Jun. 23, 2022

(51) Int. Cl.
*G02B 23/24* (2006.01)
*A61B 1/04* (2006.01)
*G02B 27/00* (2006.01)
*H04N 23/51* (2023.01)
*H04N 23/50* (2023.01)

(52) U.S. Cl.
CPC ............ *G02B 23/243* (2013.01); *A61B 1/043* (2013.01); *G02B 27/005* (2013.01); *H04N 23/51* (2023.01); *H04N 23/555* (2023.01)

(58) Field of Classification Search
CPC .... G02B 23/243; G02B 27/005; A61B 1/043; H04N 5/2252; H04N 2005/2255
USPC .......................................................... 359/434
See application file for complete search history.

(56) References Cited

U.S. PATENT DOCUMENTS

| | | | | |
|---|---|---|---|---|
| 4,735,491 A | * | 4/1988 | Takahashi | G02B 23/243 359/740 |
| 4,964,710 A | | 10/1990 | Leiner | |
| 5,684,629 A | * | 11/1997 | Leiner | G02B 13/0095 359/434 |
| 7,724,430 B2 | | 5/2010 | Kasai | |
| 9,918,619 B2 | | 3/2018 | Tesar | |

* cited by examiner

*Primary Examiner* — Marin Pichler
*Assistant Examiner* — Mitchell T Oestreich
(74) *Attorney, Agent, or Firm* — David Noel Villalpando

(57) ABSTRACT

Improved fluoresced imaging (FI) endoscope devices and systems are provided to enhance use of endoscopes with FI and visible light capabilities. An endoscope device is provided for endoscopy imaging in a white light and a fluoresced light mode. A relay system includes an opposing pair of rod lens assemblies positioned symmetrically with respect to a central airspace. The rod lens assemblies include a meniscus lens positioned immediately adjacent to a central airspace and with the convex surface facing the airspace, a first lens having positive power with a convex face positioned adjacent to the inner face of the meniscus lens, a rod lens adjacent to the first lens having positive power and an outer optical manipulating structure selected from various designs providing chromatic aberration correction.

18 Claims, 14 Drawing Sheets

ROD LENS RELAY SYSTEM WITH REDUCED CHROMATIC ABERRATION

TECHNICAL FIELD OF THE INVENTION

The invention relates generally to the field of medical image capture and more specifically to endoscope designs for improving performance fluorescent imaging and visible light imaging.

BACKGROUND OF THE INVENTION

Endoscopes and other medical scopes often use fluorescing agents or autofluorescence to better examine tissue. A fluorescing agent such as a dye may be injected or otherwise administered to tissue. Subsequently, an excitation light is directed toward the tissue. Responsive to the excitation light, the fluorescing agent fluoresces (emits light, typically at a longer wavelength than the excitation light), allowing a sensor to detect this emission light. Image data is collected by the sensor, and examining the collected images can indicate the concentration of fluorescing agent in the observed tissue. In addition, a phenomenon known as autofluorescence, in which tissue fluoresces under certain conditions without a fluorescing agent, may occur. Such autofluorescence can be detected as well. Imaging based on detected fluoresced light, known as "fluorescence imaging" (FI), is useful in medical diagnosis, testing, and many scientific fields, and may be combined with visible light imaging for many purposes including to enhance surgical precision.

A typical prior art endoscope 2, as illustrated in FIG. 1, usually includes a first imaging lens (e.g., an objective) followed by a series of carrier lenses (e.g., relays) which capture and transmit an optical image from inside an enclosed area 1 to the outside. The proximal end of the endoscope 2 may be attached, via direct coupling or an adaptor, to a camera head 3 or an eye-piece for viewing. The camera head 3 usually includes lenses for receiving the optical image and forming a real optical image onto the image sensor. The digital image captured by the image sensor can then be transmitted to a camera control unit (CCU) or other similar module for analysis and display.

Frequently, endoscopes used for FI applications, and particularly for applications involving the dye indocyanine green (ICG) are primarily designed and deployed for visible light imagery. As such, they are not typically designed to maintain a constant focus between infrared light and visible light. To perform FI imaging, such scopes often employ an appropriate optical filter to block the excitation light and transmit the fluoresced light. However, as these endoscopes are generally optimized for conventional visible light observation, due to the properties of the optical elements of the scope, including the relay lens system, the infrared fluorescence is focused at a different plane than the visible light, due to chromatic aberration occurring throughout the optical system, and primarily in the image relay system. There are existing approaches to compensate for the resulting focal differences. Camera head solutions include those wherein multiple sensors are employed, with sensors, associated with particularly wavelength bands (for example one for visible light and one for infrared light) located at different focal planes, and directed to the sensors by dichroic beam splitter. The various spectral bands are detected on the multiple sensors, each an individually appropriate focal plane, resulting in two, independently captured, in-focus images. This approach is disadvantageous due, only in part, to the complexity and cost of the necessity for multiple image sensors. Another major concern is that each individual endoscope used with such a camera head includes optics which may be particular to that make, model and manufacture of scope. Each particular endoscope will have varying amounts of chromatic error, requiring any camera head used therewith to compensate specifically for the error associated with the coupled scope. It is very difficult to construct a single camera head capable of compensating for a variety of endoscope models.

Other efforts to compensate for focal differences, such as, for example, that found in U.S. Pat. No. 8,773,756 to Tesar, et al., involve using an optical coupler that splits the light into two paths, a visible spectrum path and a NIR spectrum path. Different optical elements are used in each of the two beam paths to compensate for the chromatic focal differences. However, as with camera head solutions, such systems fail to compensate for differences between various endoscopes or to compensate for the variety of chromatic aberrations across the entire desired spectrum. For example, there is chromatic aberration, in the same direction as IR light, in the deep blue range of the visible spectrum, not addressed by Tesar, resulting in the deep blue range of the visible image being not ideally focused at the same plane as the remainder of the visible light. The dispersive properties of the optical materials used in endoscopes, and long glass paths through such optical materials, make conventional correction of the entire spectrum from deep blue to infrared particularly difficult. Finally, the chromatic aberration includes both longitudinal chromatic aberration and lateral chromatic aberration due to obliquely incident light from the object space. Techniques that employ lenses or prisms to correct for longitudinal chromatic aberration often introduce unwanted lateral chromatic aberration.

What is needed are devices and methods to enable endoscope-side solutions to issues associated with chromatic aberration of the entire spectrum from deep blue to infrared, such that such an endoscope can be attached to a generic camera head and allow the capture of in-focus visible light and FI images. What is further needed are endoscopes for fluorescence imaging applications without expensive and slow optical elements such as autofocus mechanisms or adapters and processing systems for chromatic aberration correction.

SUMMARY OF THE INVENTION

It is an object of the invention to improve correction, in endoscopic devices, of the entire spectrum from deep blue to infrared. In order to achieve this objective, various aspects of the invention provide devices and systems to enhance endoscopes for use with both FI and visible light capabilities. Relay lens systems are disclosed that compensate for chromatic aberration from the deep blue through the infrared spectrum usually utilized in visible and fluorescent imaging in endoscopic procedures. In particular, relay lens systems are disclosed which utilize fewer optical elements than has heretofore been possible. Further, some embodiments enable the use of more economical parts than possible with other state-of-the-art systems, decreasing cost as well as simplifying construction of both the relay lens systems themselves as well as the endoscopic devices in which they may be used. According to a first aspect of the invention, a relay system for an endoscope is provided. The relay system includes an opposing pair of rod lens assemblies positioned symmetrically with respect to a central airspace, wherein each rod lens assembly includes optical elements consisting essentially of a meniscus lens, a first lens, a rod lens, and an outer manipulating structure. The meniscus lens is positioned immediately adjacent to a central airspace and with the convex surface facing the airspace. The first lens has positive power with a convex face positioned adjacent to the inner face of the meniscus lens and is formed of a material having anomalous partial dispersion. The rod lens is adjacent to the first lens having positive power, and has a first face and a second face, both first and second faces being beam passing faces. The outer optical manipulating structure is selected from the group consisting of: the second face of the rod lens, being concave, positioned adjacent to a second lens having positive power and having a convex face facing the second concave face of the rod lens; the second convex face of the rod lens, being convex, positioned adjacent to an outer meniscus lens; the second face of the rod lens, being plano, positioned adjacent to a plano-convex aspherical lens; the second face of the rod lens, being plano, positioned adjacent to a positive powered lens having a convex face facing the second plano face of the rod lens with a separation gap; the second face of the rod lens, being plano, positioned adjacent to a second plano convex lens; and the second face of the rod lens, being convex. The meniscus lens, the first lens having positive power, the rod lens, and the outer optical manipulating structure together provide chromatic aberration correction by manipulating light from the blue region of the spectrum through the near IR region of the spectrum to follow the same sequence of optical surfaces and come to a common focus in a common image plane.

According to some implementations of first aspect, the first lens having positive power is plano-convex.

According to some implementations of first aspect, the first lens is manufactured from a material having an Abbe number equal to or greater than 80.

According to some implementations of first aspect, the outer optical manipulating structure is the second, concave face of the rod lens positioned adjacent to a second lens having positive power and having a convex face facing the second concave face of the rod lens. In some implementations, the second lens having positive power may be plano-convex. In some implementations, each rod lens assembly has no additional optical manipulating elements other than the those listed.

According to some implementations of first aspect, the outer optical manipulating structure is the second convex face of the rod lens positioned adjacent to an outer meniscus lens. In some implementations, each rod lens assembly has no additional optical manipulating elements other than the those listed.

According to some implementations of first aspect, the outer optical manipulating structure is the second plano face of the rod lens positioned adjacent to a plano-convex aspherical lens. In some implementations, each rod lens assembly has no additional optical manipulating elements other than the those listed.

According to some implementations of first aspect, the outer optical manipulating structure is the second plano face of the rod lens positioned adjacent to a plano-convex lens having a convex face facing the second plano face of the rod lens with a separation gap. In some implementations, each rod lens assembly has no additional optical manipulating elements other than the those listed.

According to some implementations of first aspect, the outer optical manipulating structure is the second plano face of the rod lens positioned adjacent to a second plano convex lens. In some implementations, each rod lens assembly has no additional optical manipulating elements other than the those listed.

According to some implementations of the first aspect, the outer optical manipulating structure is the second convex face of the rod lens. In some implementations, each rod lens assembly has no additional optical manipulating elements other than the those listed.

According to some implementations of the first aspect, the relay system is also corrected for astigmatism.

According to some implementations of the first aspect, the meniscus lens is constructed of a crown glass having a refractive index less than 1.65 and an Abbe number between 55 and 75

According to some implementations of the first aspect, the chromatic aberration correction is provided from approximately 400 nm to 900 nm.

According to some implementations of the first aspect, the pair of rod lens assemblies is arranged around an air space containing an aperture stop.

According to some implementations of the first aspect, the relay system also includes an endoscope containing the relay system.

According to some implementations of the first aspect, the first and second faces of the rod lens are plano.

According to a second aspect of the invention, a relay system for an endoscope includes an opposing pair of rod lens assemblies positioned symmetrically with respect a central air space, wherein each rod lens assembly includes a meniscus lens, a first lens, a rod lens, and a single outer lens. The meniscus lens is positioned adjacent to the opposing rod lens assembly. The first lens has positive optical power with a convex face positioned adjacent to an inner face of the meniscus lens. The rod lens positioned adjacent to the first plano-convex lens. The meniscus lens, the first lens having positive optical power, the rod lens, and the single outer lens together are sufficient to manipulate light to provide chromatic aberration correction by manipulating light from the blue region of the spectrum through the near IR region of the spectrum to follow the same sequence of optical surfaces through the relay system and come to a common focus in a common image plane.

According to some implementations of the second aspect, each rod lens assembly has no additional optical manipulating elements other than the those listed.

According to some implementations of the second aspect, the first lens having positive optical power is manufactured from a material having anomalous partial dispersion.

According to some implementations of the second aspect, the meniscus lens is constructed of a crown glass having a refractive index less than 1.65 and an Abbe number between 55 and 75

According to some implementations of the second aspect, the chromatic aberration correction is provided from approximately 400 nm to 900 nm.

According to some implementations of the second aspect, the relay system is also corrected for astigmatism.

According to some implementations of the second aspect, the relay system further includes an endoscope containing the relay system.

According to some implementations of the second aspect, the first and second faces of the rod lens are plano.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras and FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
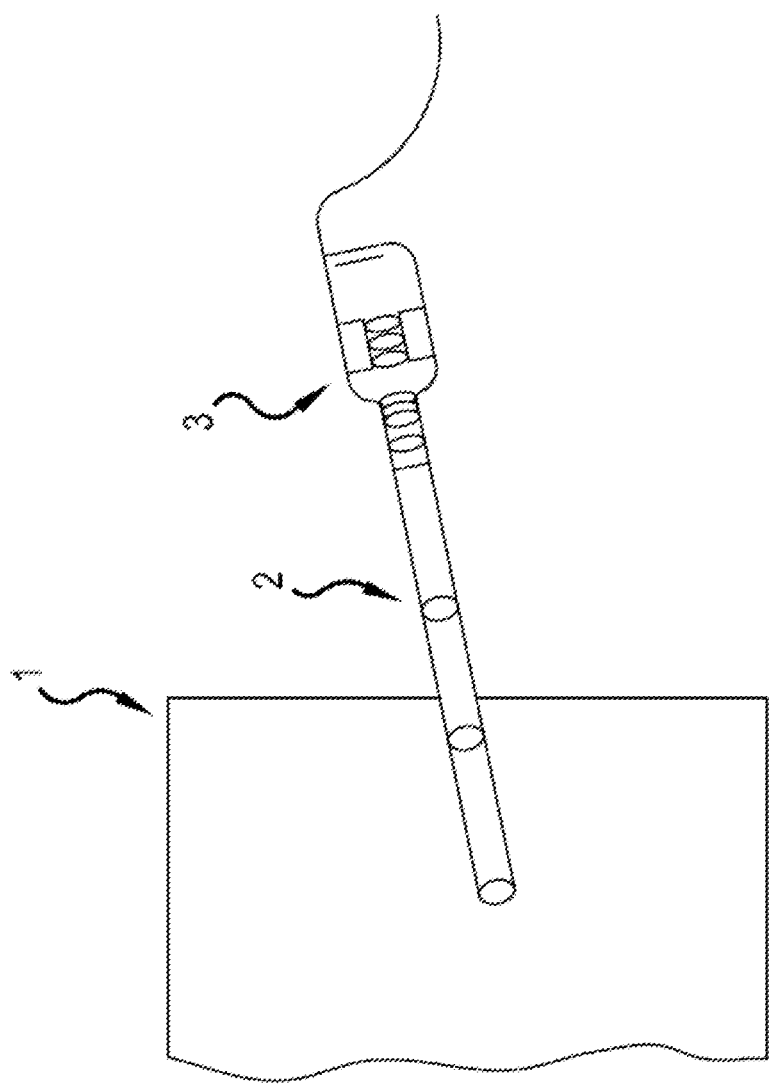
FIG. 1 is diagram of a prior art endoscopic system.
Figure 2:
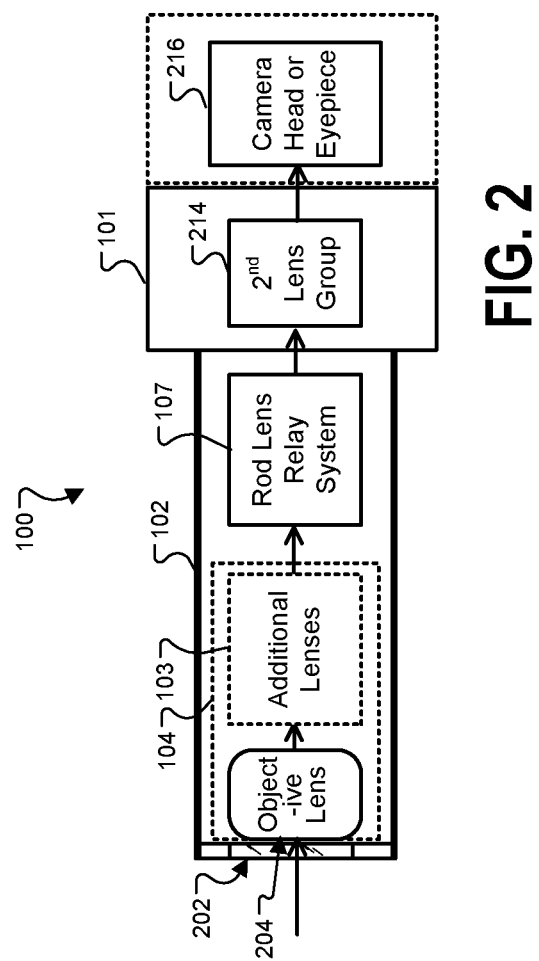
FIG. 2 is a block diagram of an endoscope device including a scope and an attached camera head.

FIG. 2 is a block diagram of an endoscope device 100 according to an example embodiment of the invention. Endoscope device 100 ("device 100", "endoscope 100") includes a shaft 102 connected to a proximal element 101. The proximal element 101 may be an eyecup including an eyepiece enabling the user to view visible light traversing the shaft 102. The eyecup may also act as an attachment element to connect the scope to a camera head 216 containing one more image sensors, via a bayonet connection, or other connection system known in the art. Alternatively the camera head element may be integrated with the shaft via the proximal element 101. Various structural components supporting the depicted elements are omitted in the diagrams herein, as well as other components such as illumination sources, fluorescent excitation sources, and controls which are known in the art and are not shown in order to avoid obscuring the relevant details of the example embodiments of the invention. At the left is shown the distal tip of the endoscope shaft 102 including a cover glass 202, which in this version faces directly along the longitudinal axis of the shaft 102, but may also be positioned at an angle relative to the longitudinal axis as is known in the art. Behind, or on the proximal side of, the cover glass 202 is shown a preferred position for the objective lens 204, usually set against or very near cover glass 202 and preferably assembled together with the cover glass in construction. While a wide angle lens is preferred for objective lens 204, this is not limiting, and any suitable lens may be used in various embodiments. Objective lens 204 may be part of an objective lens group 104 which may include one or more additional lenses 103. The particular number and arrangement of lenses in the endoscope shaft 102 will vary widely depending on the application. Optically arranged or attached at the proximal side of objective lens 204 or objective lens group 104 is rod lens relay system 107, which serves to pass the light down shaft 102 in the proximal direction. Rod lens relay system 107, including rod lens pairs, is adapted to direct the image light to create a telecentric internal image space at the proximal end of the one or more rod lenses, where a second lens group 214 is positioned as further discussed below. Also, the shaft 102 is typically rigid but shaft design variations are also known to allow rod lenses to be used in a semi-flexible shaft in which flexible joints are present in one or more places along the shaft between the rod lenses, while the shaft is rigid along the portions containing a rod lens. Such a shaft design may be used in various embodiments of the invention.

Rod lens relay system 107 functions to compensate for the chromatic aberration of the endoscope's multiple lenses such that a first portion of light having a first wavelength spectrum and a second portion of light having a second wavelength spectrum different from the first are focused onto substantially the same image plane. Assembly 214 is positioned within a telecentric internal image space proximal to rod lens relay system 107. Second lens group 214 is preferably positioned within the proximal element 101 of device 100, but may partially span the volume of the shaft 102 and the proximal element 101 or may be an element of the camera head or eyepiece 216.

Typically, rod lens relay system 107 is integrated with endoscope device 100, and, in particular, the shaft 102, and is designed to correct for chromatic aberrations. As further described below, some embodiments also provide astigmatism correction. The eyepiece, or the image sensor assembly and its associated electronics (together constituting a camera) may be integrated with the device or may be separate and detachable, such as a detachable eyepiece or a detachable camera head. In various embodiments the invention may therefore constitute an endoscopic device or an imaging system including an endoscope device 100.

Figure 3:
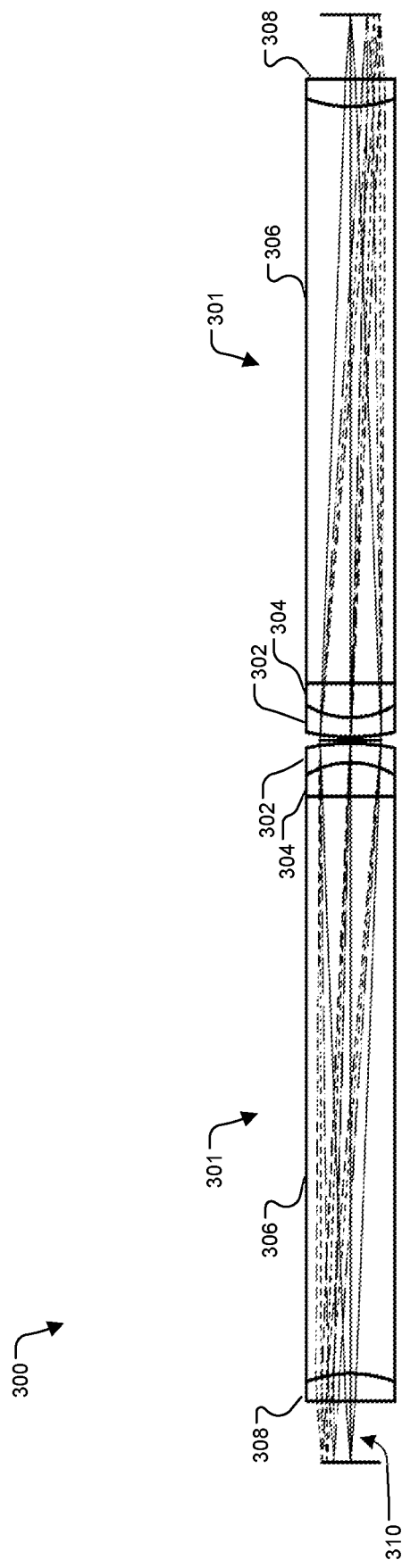
FIG. 3 is a partial cross section diagram of the optical relay system according to some embodiments of the invention for use in an endoscope device wherein all lenses are spherical, and each rod lens assembly may be fully cemented together.

FIG. 3 is a partial cross section diagram of an optical relay lens system 300 according to some embodiments to be used in an endoscope device 100. The depicted relay system 300 may be employed, for example, as rod lens relay system 107 in the system of FIG. 2. Relay system 300 includes an opposing pair of rod lens assemblies 301 positioned symmetrically with respect to a central airspace. More than one such pair may be employed in series to provide an overall relay system with a greater length. The central airspace between rod lens assemblies 301 may contain an aperture stop. This embodiment has the advantages of consisting of only four optical elements per rod lens assembly, wherein each lens is spherical, and the rod lens assembly may be fully cemented together and may have a planar outer surface, which can simplify the design and assembly of the overall relay system within the shaft 102.

Each rod lens assembly 301, according to this embodiment, includes a meniscus lens 302 positioned adjacent to the opposing rod lens assembly. A first plano-convex lens 304 has a convex face positioned adjacent to an inner face of meniscus lens 302 and a planar face at the opposite side. Other lenses may be used instead of a plano-convex lens. A rod lens 306 has a first plano surface positioned adjacent to the plano face of first plano-convex lens 304.

At the opposing, outer end of rod lens 306 is an outer optical manipulating structure which in this embodiment includes a second concave face of rod lens 306 positioned adjacent to a second plano-convex lens 308 having a convex face facing the second concave face of rod lens 306.

A light ray diagram is shown showing the path taken by light 310 passing from an object plane depicted on the left to an image plane depicted on the right. Meniscus lens 302, first plano-convex lens 304, rod lens 306, and the outer optical manipulating structure together perform chromatic aberration correction by manipulating light 310 of a spectrum from the blue region through the near IR region to have substantially the same effective optical path length and thus come to a common focus at a common image plane, allowing for simultaneous imaging throughout the spectrum. Each rod lens assembly 301 has no additional optical manipulating elements other than the those listed which together provide a chromatic aberration correction sufficient to allow simultaneous imaging of visible and IR spectrum light at the depicted common imaging plane, or sequential or separate imaging without refocusing adjustments for the visible and IR spectra. The amount of chromatic aberration correction may vary depending on the materials, sizes, and curvatures of the various optical manipulating elements. Depending on the f-number of the system, the amount of correction in focal position due to chromatic aberration sufficient to allow simultaneous imaging across the IR and visible spectrum may be less than about 15 micrometers shift across the spectral range of 400 nm to 900 nm. Additionally, depending on the number of relays in a system, this correction in focal position may vary, as associated errors accumulate over multiple relays. More preferably, a correction to a total aberration of 10 micrometers of focal shift across that range is achievable with certain embodiments employing the relay system of FIG. 3.

Meniscus lens 302 is preferably constructed with a crown glass having a refractive index less than 1.65 and an Abbe number between 55 and 75. Preferably, the first positive power lens 304, which is typically a plano-convex lens but may be another positive power lens, is constructed of a material having anomalous partial dispersion. The material of the first positive power lens 304 preferably has a lower refractive index and higher Abbe number than the material of the rod lens. For example, various types of crown glass may be used such as phosphate glasses or fluorophosphate glasses. A relatively high Abbe number is preferably used such as 55 or over. For example, various versions may employ crown glass with an Abbe number of 65, 70, 75, 80, or 85. For example, first positive power lens 304 has an Abbe number of 81.54 in some embodiments. Optical properties of the surface elements of one possible implementation of the embodiment shown in FIG. 3 are given in Table 1.

TABLE 1

Surface Data Summary for one implementation of the embodiment FIG. 3

| Surface | Radius | Thickness | Index | Abbe no. | Clear Diam |
|---|---|---|---|---|---|
| Obj | Infinity | 3.302 | Air | | 4.20 |
| 1 | Infinity | 2.0 | 1.847 | 23.78 | 6.48 |
| 2 | −7.2169 | 43.532 | 1.618 | 49.82 | 6.48 |
| 3 | Infinity | 2.5 | 1.497 | 81.55 | 6.48 |
| 4 | −6.0591 | 1.4 | 1.522 | 59.48 | 6.48 |
| 5 | −15.8891 | 0.25 | Air | | 6.48 |
| STO | Infinity | 0.25 | Air | | 4.5857 |
| 7 | 15.8891 | 1.4 | 1.522 | 59.48 | 6.48 |
| 8 | 6.0591 | 2.5 | 1.497 | 81.55 | 6.48 |
| 9 | Infinity | 43.532 | 1.618 | 49.82 | 6.48 |
| 10 | 7.2169 | 2.0 | 1.847 | 23.78 | 6.48 |
| 11 | Infinity | 3.302 | Air | | 6.48 |
| IMA | Infinity | | | | 4.2217 |

In this embodiment, as well as the embodiments described below with respect to FIG. 5, FIG. 7, and FIG. 9, the relay system also provides correction for astigmatism. As endoscope systems with rod lenses often have astigmatism, the outer optical manipulating structure of these embodiments preferably performs an astigmatism correction function.

Figure 4:
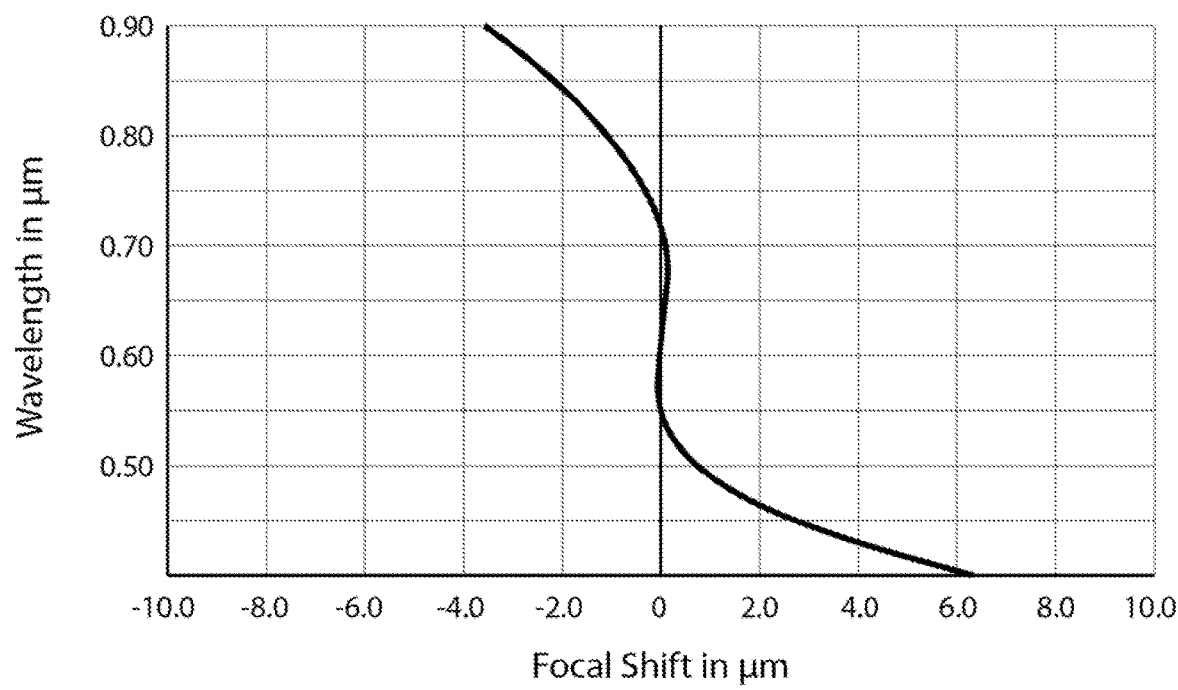
FIG. 4 is a chart showing the wavelength versus focal shift achievable with the optical relay system of FIG. 3 according to an example embodiment.

FIG. 4 is a chart showing chromatic aberration correction achievable with the relay system of FIG. 3 according to an example implementation with the properties shown in Table 1. The vertical axis shows the light wavelength in micrometers from 0.4 to 0.9 (400 to 900 nanometers), and the horizontal axis shows the focal shift provided by the relay system using a single pair of rod lens assemblies 301 in an endoscope optical assembly. As can be seen on the chart, the focal shift is about 6 micrometers at the 405 nanometer wavelength and exhibits a curve to about negative 4 micrometers of focal shift at the 900 nanometer wavelength, for a total focal shift range of about 10 micrometers across the depicted spectrum. This focal shift provided by the inventive optical relay system minimizes the variance of focal position as a function of wavelength which would ordinarily be present due to chromatic aberration of a conventional rod lens relay pair.

Figure 5:
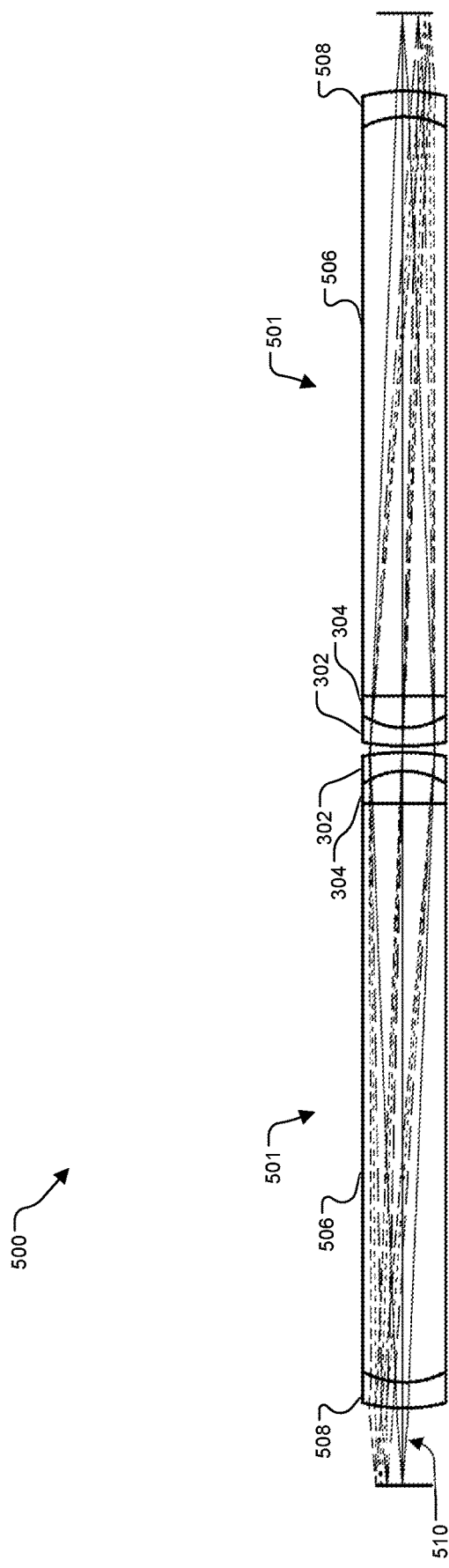
FIG. 5 is a partial cross section diagram of the optical relay system of the invention for use in an endoscope device wherein all lenses are spherical, and each rod lens assembly may be fully cemented together according to additional embodiments.

FIG. 5 is a partial cross section diagram of an optical relay lens system 500 according to some additional embodiments to be used in an endoscope device 100. A light ray diagram is overlaid on the diagram. Relay system 500 includes an opposing pair of rod lens assemblies 501 positioned symmetrically with respect to a central airspace. As with the embodiments of FIG. 3, more than one such pair may be employed in series to provide an overall relay system with a greater length. The central airspace between rod lens assemblies 501 may contain an aperture stop. This embodiment has the advantages of consisting of only four optical elements per rod lens assembly, wherein each lens is spherical, and the rod lens assembly may be fully cemented together, which can simplify the design and assembly of the overall relay system within the shaft 102.

Each rod lens assembly 501 includes a meniscus lens 302 and a first plano-convex lens 304, or other positive power lens, similar to those described with respect to FIG. 3. In this embodiment, a rod lens 506 is a plano-convex rod lens having has a first plano surface positioned adjacent to the plano face of first plano-convex lens 304. At the opposing, outer end of rod lens 506 is an outer optical manipulating structure which includes a second convex face of rod lens 506 positioned adjacent to an outer meniscus lens 508.

Meniscus lens 302, first plano-convex lens 304, rod lens 506, and the outer optical manipulating structure together perform chromatic aberration correction by manipulating light 510 in the blue region of the spectrum through the near IR region of the spectrum to have the same effective optical path length so as to come to a common focus at a common image plane. Each rod lens assembly 501 has no additional optical manipulating elements other than the those listed which together provide a chromatic aberration correction sufficient to allow simultaneous imaging of visible and IR spectrum light at the depicted common imaging plane, or sequential or separate imaging without refocusing adjustments for the visible spectrum and IR. Optical properties of the surface elements of an implementation of the embodiment shown in FIG. 5 are given in Table 2.

TABLE 2

Surface Data Summary for one implementation of the embodiment shown in FIG. 5

| Surface | Radius | Thickness | Index | Abbe no. | Clear Diam |
|---|---|---|---|---|---|
| Obj | Infinity | 6.0 | Air | | 4.2 |
| 1 | 13.2864 | 2.0 | 1.847 | 23.78 | 6.48 |
| 2 | 6.5539 | 44.835 | 1.618 | 49.82 | 6.48 |
| 3 | Infinity | 2.5 | 1.497 | 81.55 | 6.48 |
| 4 | −5.8150 | 1.4 | 1.512 | 70.86 | 6.48 |
| 5 | −17.8746 | 0.25 | Air | | 6.48 |
| STO | Infinity | 0.25 | Air | | 5.3157 |
| 7 | 17.8746 | 1.4 | 1.512 | 70.86 | 6.48 |
| 8 | 5.8150 | 2.5 | 1.497 | 81.55 | 6.48 |
| 9 | Infinity | 44.835 | 1.618 | 49.82 | 6.48 |
| 10 | −6.5539 | 2.0 | 1.847 | 23.78 | 6.48 |
| 11 | −13.2864 | 6.0 | Air | | 6.48 |
| IMA | Infinity | | | | 4.2209 |

Figure 6:
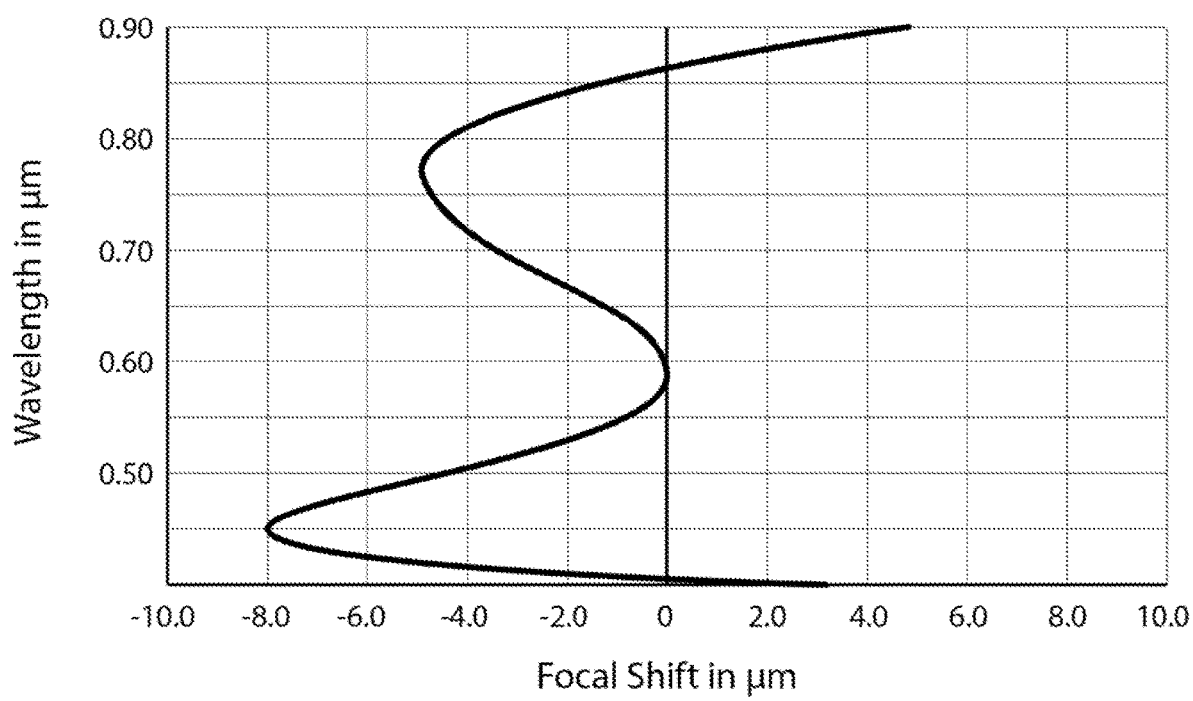
FIG. 6 is a chart showing the wavelength versus focal shift achievable by the optical relay system of FIG. 5 according to an example embodiment.

FIG. 6 is a chart showing chromatic aberration correction achievable with the relay system of FIG. 5 according to an example implementation with the properties shown in Table 2. As can be seen, the range of focal shift across the spectrum from 405 to 900 nanometers varies from a minus 8 micrometer shift to about 5 micrometers, for a total range of approximately 13 micrometers. This focal shift provided by the inventive optical relay system minimizes the variance of focal position as a function of wavelength which would ordinarily be present due to chromatic aberration of a conventional rod lens relay pair.

Figure 7:
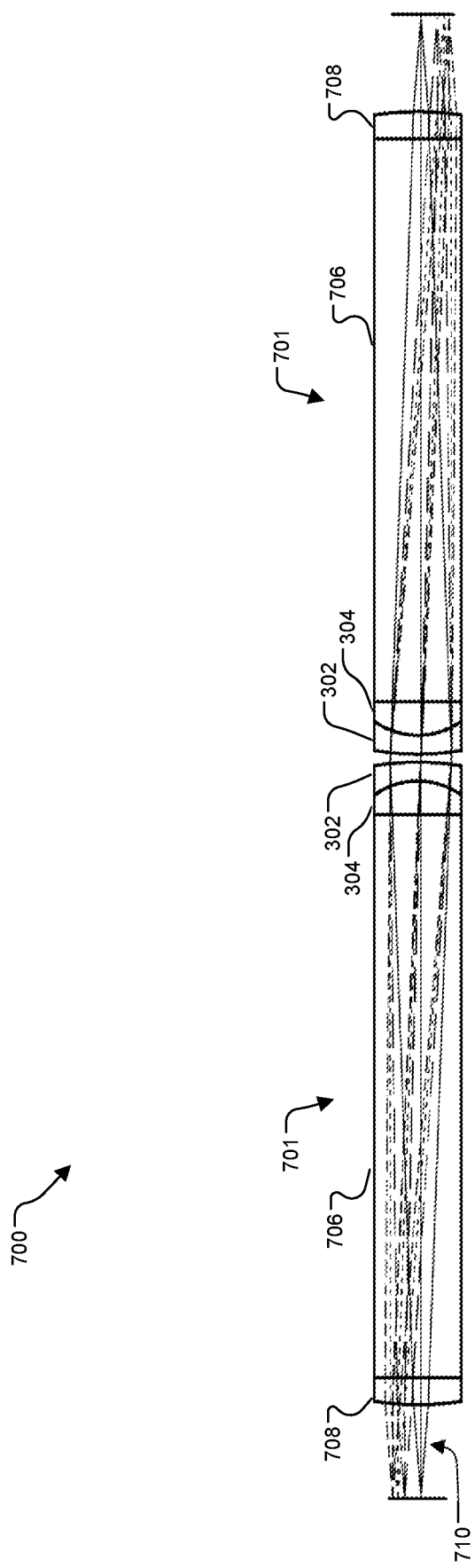
FIG. 7 is a partial cross section diagram showing an optical relay system according to an embodiment where the rod lens element is planar on both ends and the rod lens assembly may be completely cemented together.

FIG. 7 is a partial cross section diagram of an optical relay lens system 700 according to additional embodiments to be used in an endoscope device 100. In this embodiment, and that of FIG. 9, the rod lenses 706 are plano-plano rod lenses which provide lower construction costs compared to rod lenses having curved faces. Relay system 700 includes an opposing pair of rod lens assemblies 701 positioned symmetrically with respect to a central airspace. As with the embodiments of FIG. 3, more than one such pair may be employed in series to provide an overall relay system with a greater length. The central airspace between rod lens assemblies 301 may contain an aperture stop. This embodiment has the advantages, beyond that of the planar-planar rod lens element, of consisting of only four optical elements per rod lens assembly and the rod lens assembly may be fully cemented together, which can simplify the design and assembly of the overall relay system within the shaft 102.

A light ray diagram is overlaid on the diagram showing light passing from the object plane depicted on the left to an image plane depicted on the right. As with the other embodiments herein, additional pairs rod lens assemblies 701 may be placed end to end with the depicted pair of assemblies, with the image plane at which an image is measured with a sensor positioned after the final pair of rod lens assemblies.

Each rod lens assembly 701 includes a meniscus lens 302 and a first plano-convex lens 304, or other positive power lens, similar to those described with respect to FIG. 3. In this embodiment, a rod lens 706 is a plano-plano rod lens having has a first plano surface positioned adjacent to the plano face of first plano-convex lens 304. At the opposing, outer end of rod lens 706 is an outer optical manipulating structure which includes a second plano face of rod lens 706 positioned adjacent to a plano-convex aspherical lens 708. The use of an aspheric lens in this embodiment provides ability to correct for astigmatism while using a lower cost plano-plano rod lens.

Meniscus lens 302, first plano-convex lens 304, rod lens 706, and the outer optical manipulating structure together perform chromatic aberration correction by manipulating light 710 in the blue region of the spectrum through the near IR region of the spectrum to have the same effective optical path length, and thus come to a common focus at a common image plane. Each rod lens assembly 701 has no additional optical manipulating elements other than the those listed which together provide a chromatic aberration correction sufficient to allow simultaneous imaging of visible and IR spectrum light at the depicted common imaging plane, or sequential or separate imaging without refocusing adjustments for the visible spectrum and IR. Optical properties of the surface elements of an implementation of the embodiment shown in FIG. 7 are given in Table 3.

TABLE 3

Surface Data Summary for one implementation of the embodiment shown in FIG. 7

| Surface | Radius | Thickness | Index | Abbe no. | Clear Diam | Conic |
|---|---|---|---|---|---|---|
| Obj | Infinity | 6.995 | Air | | 4.2 | 0 |
| 1 | 20.8646 | 2.0 | 1.717 | 29.52 | 6.48 | −5.6347 |
| 2 | Infinity | 41.805 | 1.618 | 49.82 | 6.48 | 0 |
| 3 | Infinity | 2.5 | 1.529 | 76.98 | 6.48 | 0 |
| 4 | −5.5174 | 1.4 | 1.540 | 59.71 | 6.48 | 0 |
| 5 | −19.4448 | 0.3 | Air | | 6.48 | 0 |
| STO | Infinity | 0.3 | Air | | 4.5372 | 0 |
| 7 | 19.4448 | 1.4 | 1.540 | 59.71 | 6.48 | |
| 8 | 5.5174 | 2.5 | 1.529 | 76.98 | 6.48 | 0 |
| 9 | Infinity | 41.805 | 1.618 | 49.82 | 6.48 | 0 |
| 10 | Infinity | 2.0 | 1.717 | 29.52 | 6.48 | 0 |
| 11 | −20.8646 | 6.995 | Air | | 6.48 | −5.6347 |
| IMA | Infinity | | | | 4.2247 | 0 |

Figure 8:
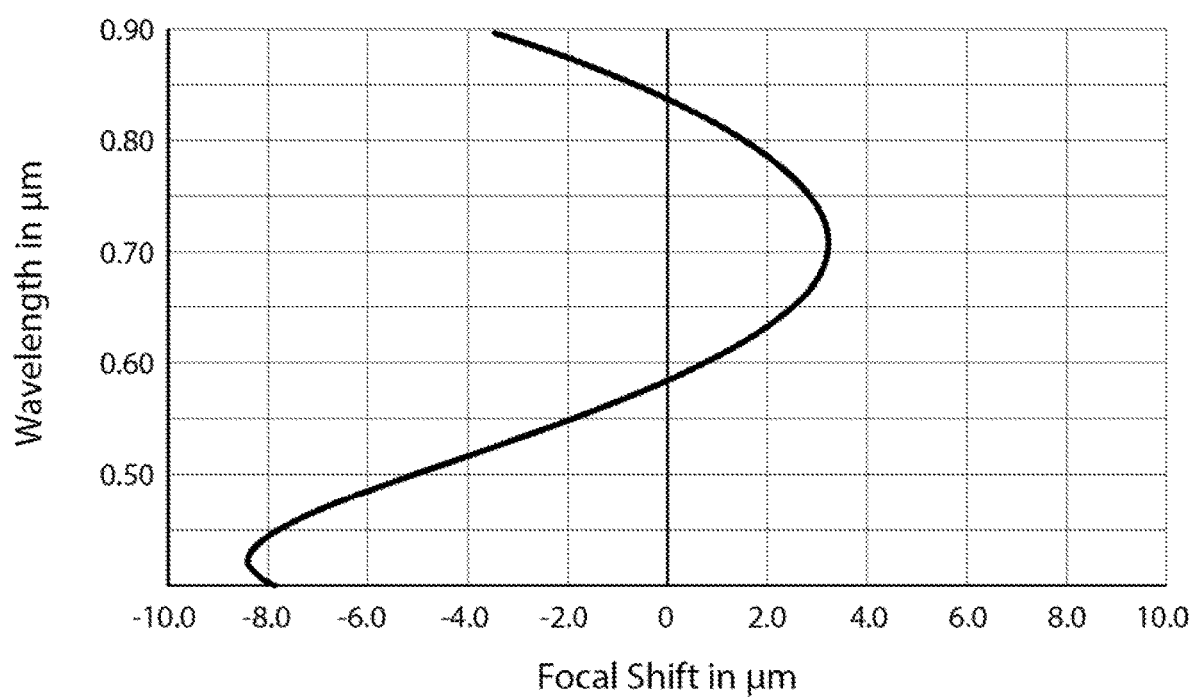
FIG. 8 is a chart showing the wavelength versus focal shift achievable by the optical relay system of FIG. 7 according to an example embodiment.

FIG. 8 is a chart showing chromatic aberration correction achievable with the relay system of FIG. 7 according to an example implementation with the properties shown in Table 3. The focal shift ranges from slightly larger than negative 8 micrometers at the 405 nanometer wavelength, to about positive 3 micrometers around 700 nanometers, providing a total focal shift range of about 11 micrometers. This focal shift provided by the inventive optical relay system minimizes the variance of focal position as a function of wavelength which would ordinarily be present due to chromatic aberration of a conventional rod lens relay pair.

Figure 9:
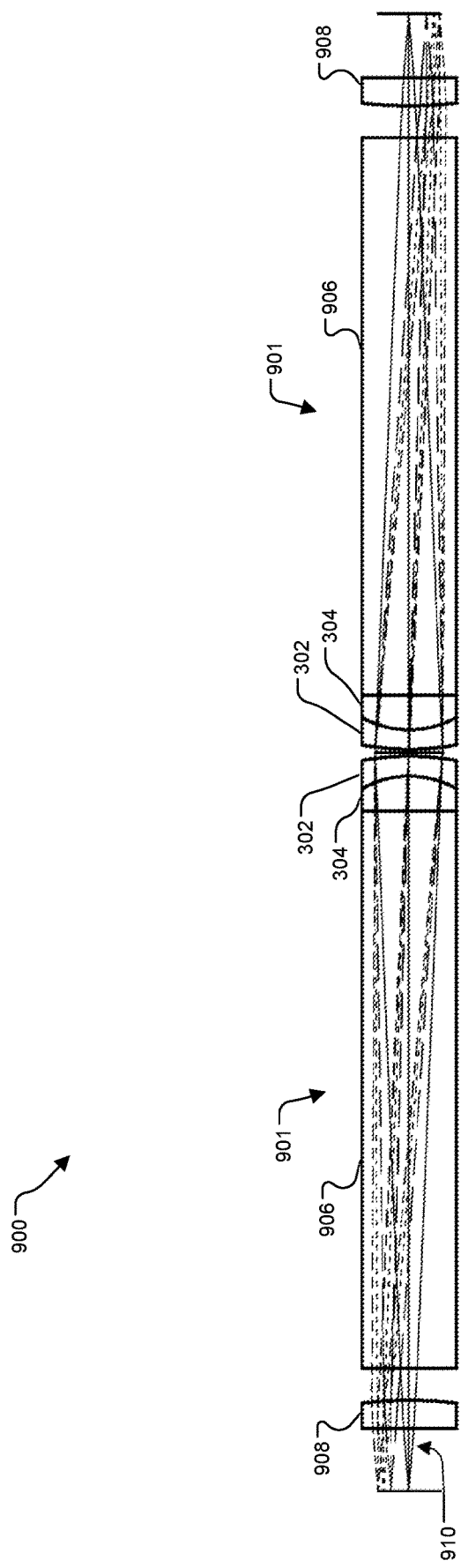
FIG. 9 is a partial cross section diagram showing an optical relay system according to embodiments where the rod lens element is planar on both ends and all lens elements are spherical, including detached elements.

FIG. 9 is a partial cross section diagram of an optical relay lens system 900 according to additional embodiments to be used in an endoscope device 100. Relay system 900 includes an opposing pair of rod lens assemblies 901 positioned symmetrically with respect to a central airspace. As with the embodiments discussed above, more than one such pair may be employed in series to provide an overall relay system with a greater length. The central airspace between rod lens assemblies 301 may contain an aperture stop. This embodiment has the advantages, beyond that of the planar-planar rod lens element, of consisting of only four optical elements per rod lens assembly and all of the lenses are spherical.

A light ray diagram is overlaid on the diagram showing light passing from the object plane depicted on the left to an image plane depicted on the right. Additional pairs of rod lens assemblies 901 may be placed end to end with the depicted pair of assemblies, with the image plane at which an image is measured with a sensor positioned after the final pair of rod lens assemblies.

Each rod lens assembly 901 includes a meniscus lens 302 and a first plano-convex lens 304, or other positive power lens, like those of FIG. 3. In this embodiment, a rod lens 906 is a plano-plano rod lens having has a first plano surface positioned adjacent to the plano face of first plano-convex lens 304. At the opposing, outer end of rod lens 906 is an outer optical manipulating structure which includes a second plano face of the rod lens positioned adjacent to a plano-convex lens 908 having a convex face facing the second plano face of the rod lens with a separation gap. Other lenses with a positive power may be used in place of plano-convex lens 908. This embodiment also provides ability to correct for astigmatism while using a low cost plano-plano rod lens in the relay system.

Meniscus lens 302, first plano-convex lens 304, rod lens 906, and the outer optical manipulating structure 908 together perform chromatic aberration correction by manipulating light 910 in the blue region of the spectrum through the near IR region of the spectrum to have the same effective optical path length, and thus and come to a common focus at a common image plane. Each rod lens assembly 901 has no additional optical manipulating elements other than the those listed which together provide a chromatic aberration correction sufficient to allow simultaneous imaging of visible and IR spectrum light at the depicted common imaging plane, or sequential or separate imaging without refocusing adjustments for the visible spectrum and IR. Optical properties of the surface elements of an implementation of the embodiment shown in FIG. 9 are given in Table 4.

TABLE 4

Surface data summary for one implementation of the embodiment shown in FIG. 9

| Surface | Radius | Thickness | Index | Abbe no. | Clear Diam |
|---|---|---|---|---|---|
| Obj | Infinity | 4.553 | Air | | 4.2 |
| 1 | Infinity | 2.0 | 1.923 | 18.90 | 6.48 |
| 2 | −27.8072 | 2.284 | Air | | 6.48 |
| 3 | Infinity | 39.966 | 1.618 | 49.82 | 6.48 |
| 4 | Infinity | 2.5 | 1.497 | 81.55 | 6.48 |
| 5 | −6.2398 | 1.4 | 1.523 | 59.48 | 6.48 |
| 6 | −16.6953 | 0.25 | Air | | 6.48 |
| STO | Infinity | 0.25 | Air | | 4.5853 |
| 8 | 16.6953 | 1.4 | 1.523 | 59.48 | 6.48 |
| 9 | 6.2398 | 2.5 | 1.497 | 81.55 | 6.48 |
| 10 | Infinity | 39.996 | 1.618 | 49.82 | 6.48 |
| 11 | Infinity | 2.284 | Air | | 6.48 |
| 12 | 27.8073 | 2.0 | 1.923 | 18.90 | 6.48 |
| 13 | Infinity | 4.553 | Air | | 6.48 |
| IMA | Infinity | | | | 4.2233 |

Figure 10:
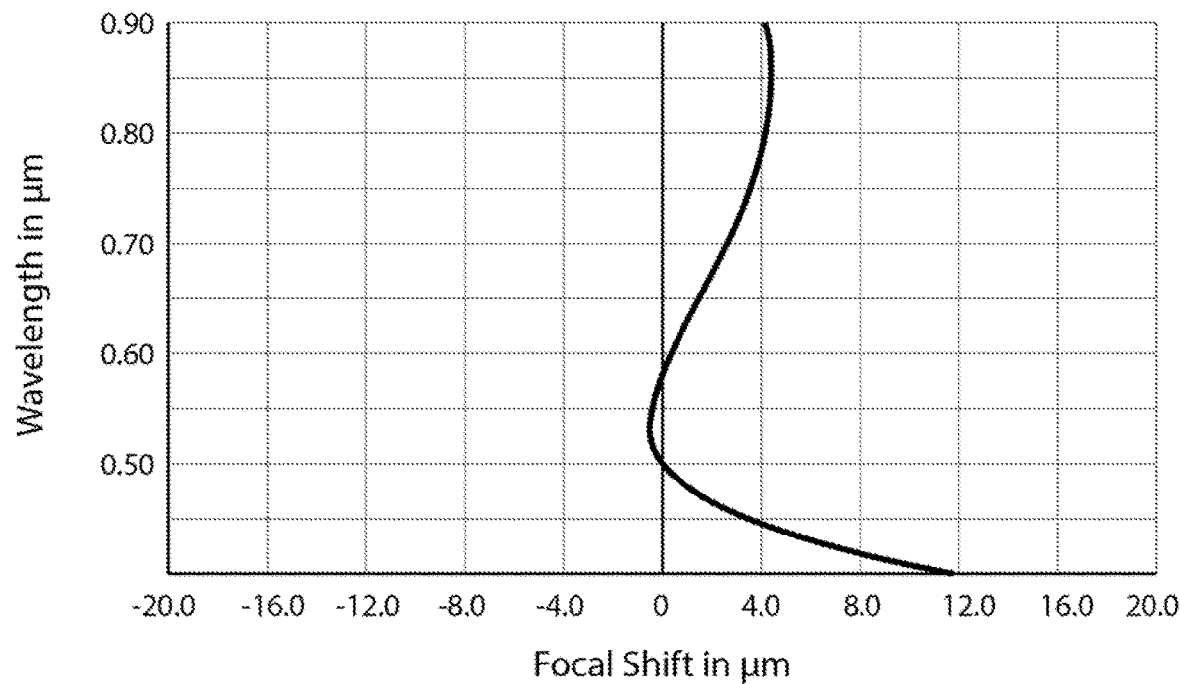
FIG. 10 is a chart showing the wavelength versus focal shift achievable by the optical relay system of FIG. 9 according to an example embodiment.

FIG. 10 is a chart showing chromatic aberration correction achievable with the relay system of FIG. 9 according to an example implementation with the properties shown in Table 3. The focal shift ranges from 12 micrometers at the 405 nanometer wavelength, to slightly under zero micrometers at 550 nanometers, providing a total focal shift range of about 12 micrometers.

Figure 11:
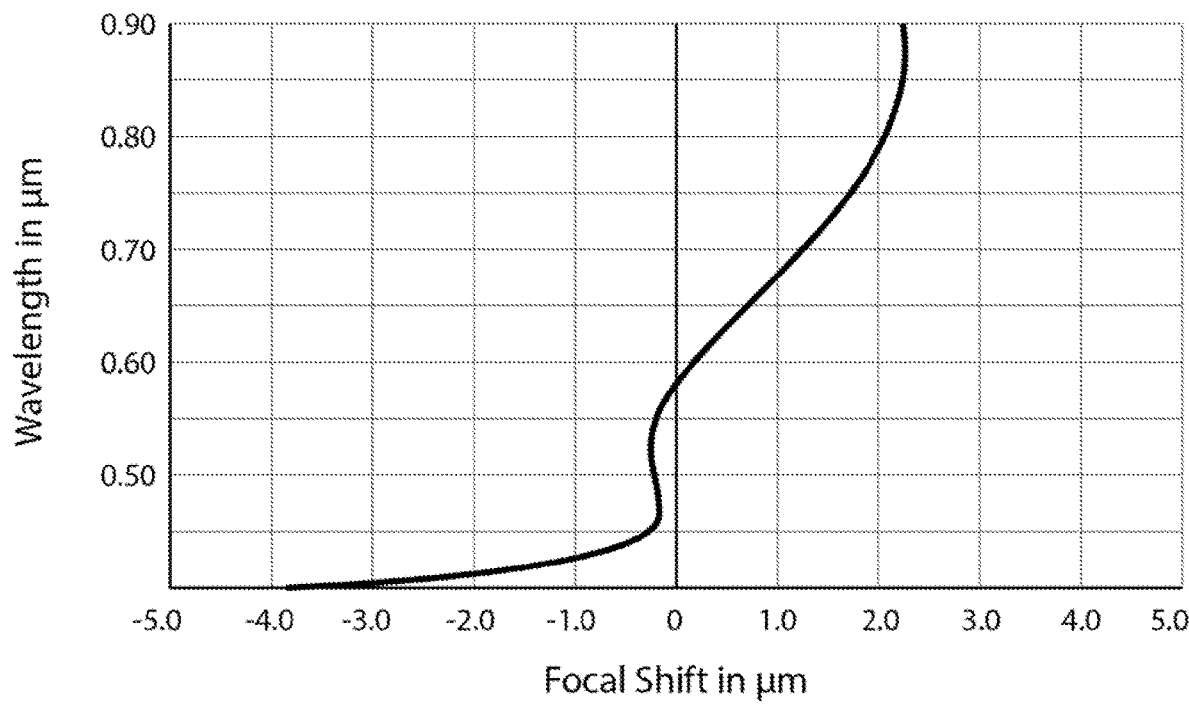
FIG. 11 is another chart showing the wavelength versus focal shift achievable by the optical relay system according to another embodiment of the arrangement of FIG. 9, using optical elements with different focal powers from the embodiment of FIG. 10.

FIG. 11 is another chart showing chromatic aberration achievable according to another implementation of the embodiment of FIG. 9 using elements with different properties (shown in Table 5) from the embodiment of FIG. 10. In this version, the focal shift ranges from about negative 4 micrometers at 405 nanometers, to slightly over two micrometers at 900 nanometers, for a total focal shift range of slightly over 6 micrometers. This focal shift provided by the inventive optical relay system minimizes the variance of focal position as a function of wavelength which would ordinarily be present due to chromatic aberration of a conventional rod lens relay pair.

TABLE 5

Alternative surface data summary for one implementation of the embodiment shown in FIG. 9

| Surface | Radius | Thickness | Index | Abbe no. | Clear Diam |
|---|---|---|---|---|---|
| Obj | Infinity | 6.3133 | Air | | 4.2 |
| 1 | 102.5046 | 2.0 | 1.923 | 18.90 | 6.48 |
| 2 | −34.8825 | 0.25 | Air | | 6.48 |
| 3 | Infinity | 40.2717 | 1.620 | 36.37 | 6.48 |
| 4 | Infinity | 2.5 | 1.497 | 81.55 | 6.48 |
| 5 | −6.2200 | 1.4 | 1.522 | 59.48 | 6.48 |
| 6 | −17.0677 | 0.25 | Air | | 6.48 |
| STO | Infinity | 0.25 | Air | | 4.3345 |
| 8 | 17.0677 | 1.4 | 1.522 | 59.48 | 6.48 |
| 9 | 6.2200 | 2.5 | 1.497 | 81.55 | 6.48 |

TABLE 5-continued

Alternative surface data summary for one implementation of the embodiment shown in FIG. 9

| Surface | Radius | Thickness | Index | Abbe no. | Clear Diam |
|---|---|---|---|---|---|
| 10 | Infinity | 40.2717 | 1.620 | 36.37 | 6.48 |
| 11 | Infinity | 0.25 | Air | | 6.48 |
| 12 | 34.8825 | 2.0 | 1.923 | 18.90 | 6.48 |
| 13 | −102.5046 | 6.3133 | Air | | 6.48 |
| IMA | Infinity | | | | 4.2 |

Figure 12:
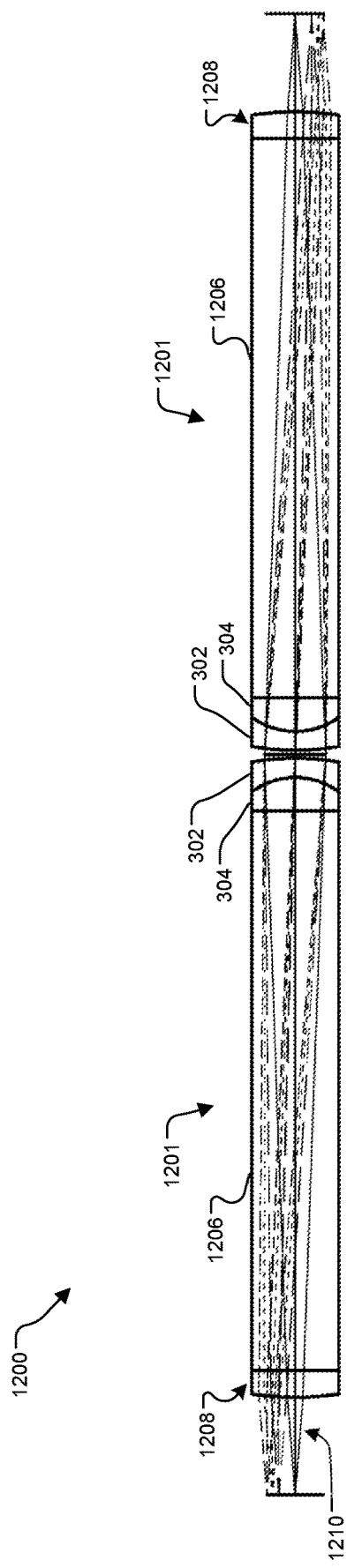
FIG. 12 is a partial cross section diagram of an optical relay system according to additional embodiments.

FIG. 12 is a partial cross section diagram of an optical relay lens system 1200 according to additional embodiments to be used in an endoscope device 100. Relay system 1200 includes an opposing pair of rod lens assemblies 1201 positioned symmetrically with respect to a central airspace. As with the embodiments discussed above, more than one such pair may be employed in series to provide an overall relay system with a greater length. The central airspace between rod lens assemblies 1201 may contain an aperture stop. While, as opposed to the embodiments shown above, this embodiment does not explicitly correct for astigmatism, it offers a simplified design, employing a plano-plano rod lens, consists of only four optical elements per rod lens assembly, and all of the lenses are spherical and may be cemented together into a single unit.

A light ray diagram is overlaid on the diagram showing light passing from the object plane depicted on the left to an image plane depicted on the right. Additional pairs rod lens assemblies 1201 may be placed end to end with the depicted pair of assemblies, with the image plane at which an image is measured with a sensor positioned after the final pair of rod lens assemblies.

Each rod lens assembly 1201 includes a meniscus lens 302 and a positive power lens such as first plano-convex lens 304 like that of FIG. 3. In this embodiment, a rod lens 1206 is a plano-plano rod lens having has a first plano surface positioned adjacent to the plano face of first plano-convex lens 304. At the opposing, outer end of rod lens 1206 is an outer optical manipulating structure which includes a second plano face of the rod lens positioned adjacent to a plano-convex lens 1208 having a plano face adjacent to rod lens 1206 and a convex face directed outward.

Meniscus lens 302, first plano-convex lens 304, rod lens 1206, and the outer optical manipulating structure together perform chromatic aberration correction by manipulating light 1210 in the blue region of the spectrum through the near IR region of the spectrum to have substantially the same effective optical path length, and therefore come to a common focus at a common image plane. Each rod lens assembly 1201 has no additional optical manipulating elements other than the those listed which together provide a chromatic aberration correction sufficient to allow simultaneous imaging of visible and IR spectrum light at the depicted common imaging plane, or separate or sequential imaging without refocusing adjustments for the visible spectrum and IR.

Figure 13:
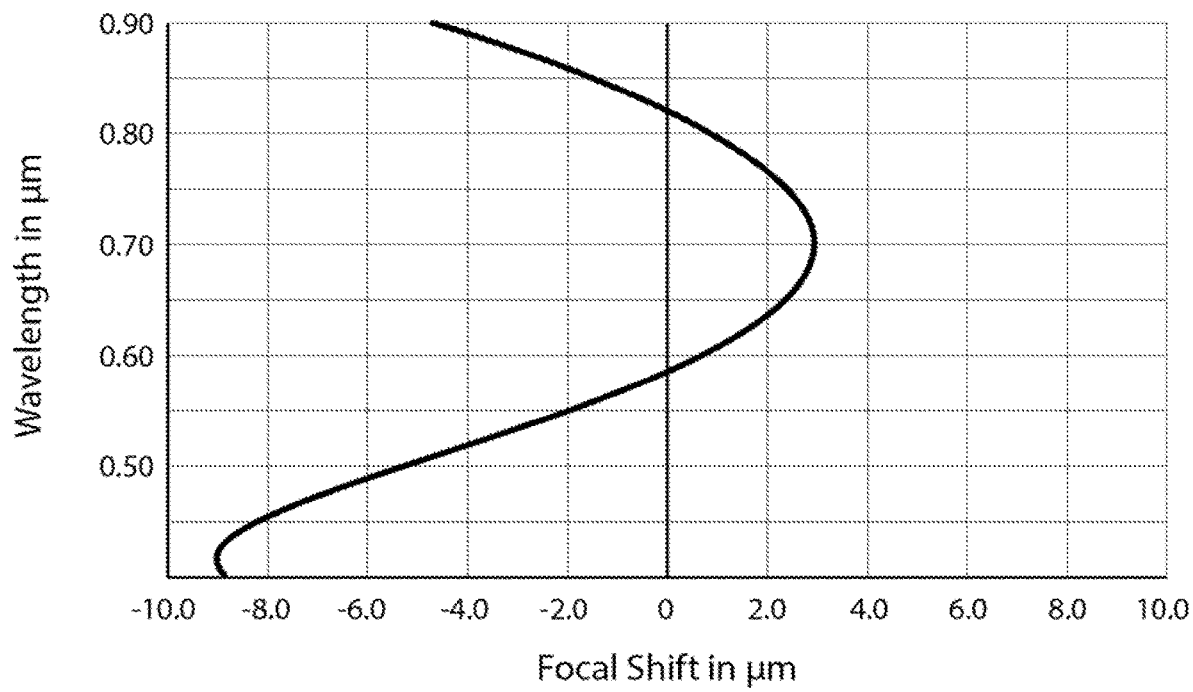
FIG. 13 is a chart showing the wavelength versus focal shift achievable by the optical relay system of FIG. 12 according to an example embodiment.
Figure 14:
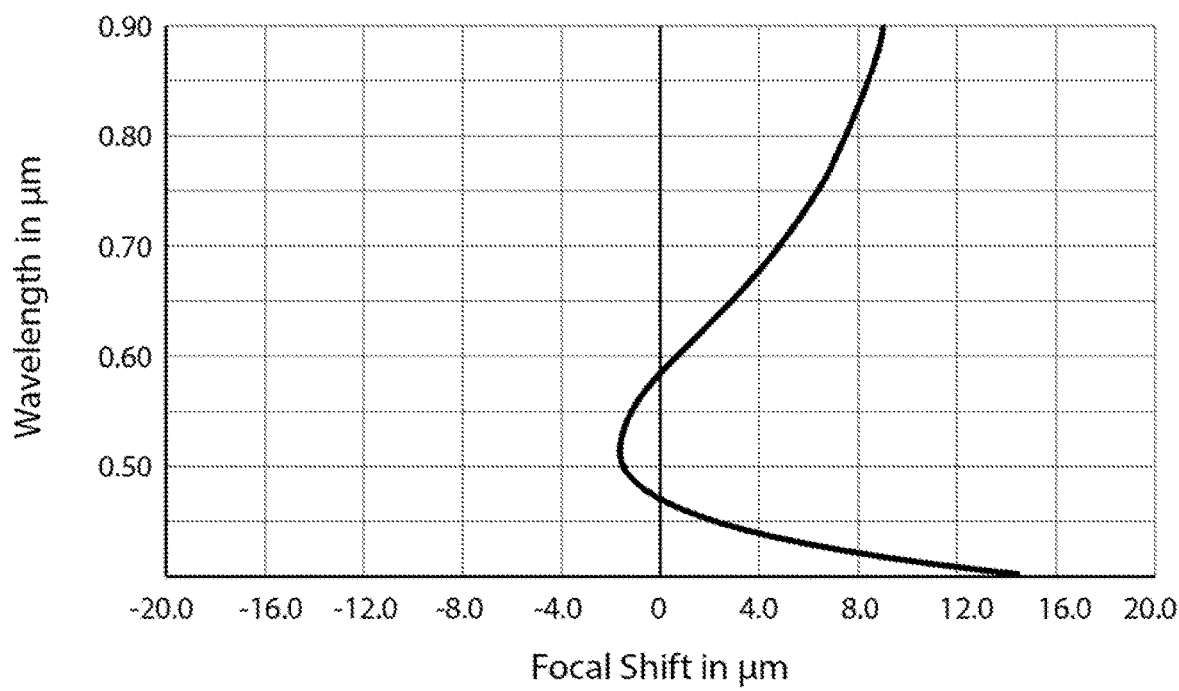
FIG. 14 is another chart showing the wavelength versus focal shift achievable by the optical relay system according to another embodiment of the arrangement of FIG. 12 using optical elements with different focal powers from the embodiment of FIG. 13.

FIGS. 13 and 14 are charts showing chromatic aberration correction achievable with implementations of the relay system of FIG. 12. FIG. 13, with corresponding surface properties given in Table 6, shows a focal shift range from about negative 9 micrometers at the 405 nanometer wavelength, to about 3 micrometers at 700 nanometers, providing a total focal shift range of about 12 micrometers. FIG. 14, with corresponding surface properties given in Table 7, shows a focal shift rang from about 14 micrometers at 405 nanometers, to about negative two micrometers at around 500 nanometers, for a total focal shift range of 16 micrometers. This focal shift provided by the inventive optical relay system minimizes the variance of focal position as a function of wavelength which would ordinarily be present due to chromatic aberration of a conventional rod lens relay pair.

TABLE 6

Surface Data Summary for one implementation of the embodiment shown in FIG. 12

| Surface | Radius | Thickness | Index | Abbe no. | Clear Diam |
|---|---|---|---|---|---|
| Obj | Infinity | 7.257 | Air | | 4.2 |
| 1 | 21.3368 | 2.0 | 1.717 | 29.52 | 6.48 |
| 2 | Infinity | 41.543 | 1.618 | 49.82 | 6.48 |
| 3 | Infinity | 2.5 | 1.529 | 76.98 | 6.48 |
| 4 | −5.4641 | 1.4 | 1.540 | 59.71 | 6.48 |
| 5 | −19.5366 | 0.3 | Air | | 6.48 |
| STO | Infinity | 0.3 | Air | | 4.5429 |
| 7 | 19.5366 | 1.4 | 1.540 | 59.71 | 6.48 |
| 8 | 5.4641 | 2.5 | 1.529 | 76.98 | 6.48 |
| 9 | Infinity | 41.543 | 1.618 | 49.82 | 6.48 |
| 10 | Infinity | 2.0 | 1.718 | 29.52 | 6.48 |
| 11 | −21.3368 | 7.257 | Air | | 6.48 |
| IMA | Infinity | | | | 4.2695 |

TABLE 7

Surface Data Summary for an alternative implementation of the embodiment shown in FIG. 12

| Surface | Radius | Thickness | Index | Abbe no. | Clear Diam |
|---|---|---|---|---|---|
| Obj | Infinity | 4.716 | Air | | 4.2 |
| 1 | 25.0813 | 2.0 | 1.801 | 34.97 | 6.48 |
| 2 | Infinity | 44.083 | 1.618 | 49.82 | 6.48 |
| 3 | Infinity | 2.5 | 1.439 | 94.66 | 6.48 |
| 4 | −7.6413 | 1.4 | 1.569 | 63.10 | 6.48 |
| 5 | −13.1283 | 0.3 | Air | | 6.48 |
| STO | Infinity | 0.3 | Air | | 4.8458 |
| 7 | 13.1283 | 1.4 | 1.569 | 63.10 | 6.48 |
| 8 | 7.6413 | 2.5 | 1.439 | 94.66 | 6.48 |
| 9 | Infinity | 44.083 | 1.618 | 49.82 | 6.48 |
| 10 | Infinity | 2.0 | 1.801 | 34.97 | 6.48 |
| 11 | −25.0813 | 4.716 | Air | | 6.48 |
| IMA | Infinity | | | | 4.2545 |

Figure 15:
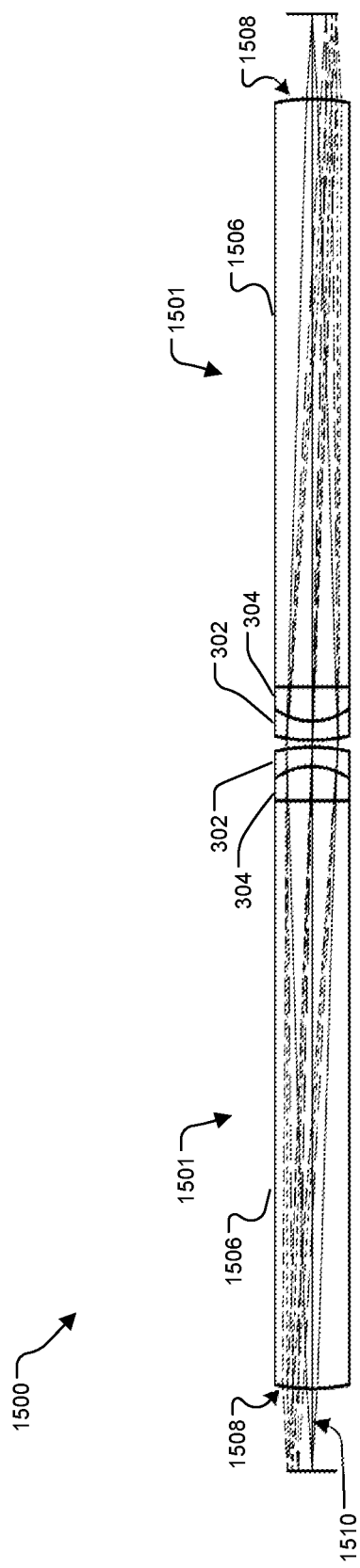
FIG. 15 is a partial cross section diagram of an optical relay system according to additional embodiments.

FIG. 15 is a partial cross section diagram of an optical relay lens system 1500 according to additional embodiments to be used in an endoscope device 100. Relay system 1500 includes an opposing pair of rod lens assemblies 1501 positioned symmetrically with respect to a central airspace. As with the embodiments discussed above, more than one such pair may be employed in series to provide an overall relay system with a greater length. As with the embodiment shown in FIG. 12, this embodiment does not explicitly correct for astigmatism, however it offers a simplified design, employing only three optical elements per rod lens assembly, and all of the lenses may be cemented together into a single unit.

A light ray diagram is overlaid on the diagram showing light passing from the object plane depicted on the left to an image plane depicted on the right. Additional pairs rod lens assemblies 1501 may be placed end to end with the depicted pair of assemblies, with the image plane at which an image is measured with a sensor positioned after the final pair of rod lens assemblies.

Each rod lens assembly 1501 includes a meniscus lens 302 and a positive power lens such as first plano-convex lens 304 like that of FIG. 3. In this embodiment, a rod lens 1506 is a plano-convex rod lens having has a first plano surface positioned adjacent to the plano face of first plano-convex lens 304. At the opposing, outer end of rod lens 1506 is an outer optical manipulating structure which includes a convex face of the rod lens directed outward.

Meniscus lens 302, first plano-convex lens 304, rod lens 1506, and the outer optical manipulating structure together perform chromatic aberration correction by manipulating light 1510 in the blue region of the spectrum through the near IR region of the spectrum to have the same effective optical path length, and thus come to a common focus at a common image plane. Each rod lens assembly 1501 has no additional optical manipulating elements other than the those listed which together provide a chromatic aberration correction sufficient to allow simultaneous imaging of visible and IR spectrum light at the depicted common imaging plane, or separate or sequential imaging without refocusing adjustments for the visible spectrum and IR.

Figure 16:
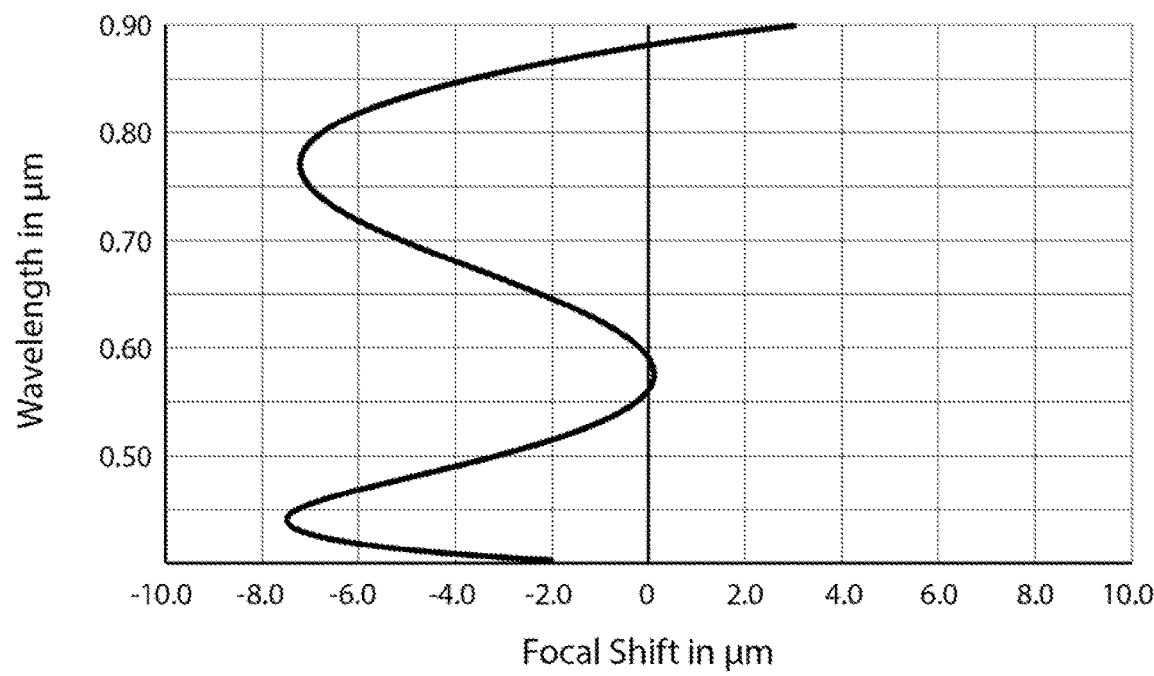
FIG. 16 is a chart showing the wavelength versus focal shift achievable by the optical relay system of FIG. 15 according to an example embodiment.
Figure 17:
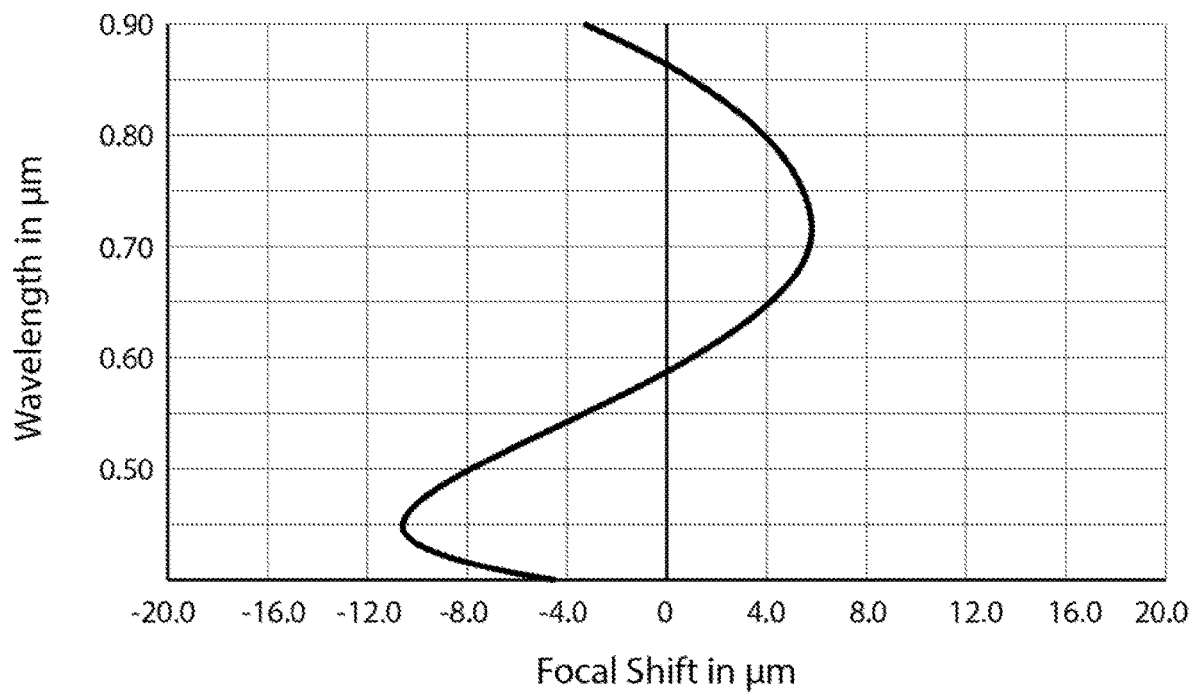
FIG. 17 is another chart showing the wavelength versus focal shift achievable by the optical relay system of FIG. 15 using optical elements with different focal powers from the embodiment of FIG. 16.

FIGS. 16 and 17 are charts showing chromatic aberration correction achievable with implementations of the relay system of FIG. 15. FIG. 16, with corresponding surface properties given in Table 8 shows a focal shift range from about negative 7 micrometers at the 475 nanometer wavelength, to about 3 micrometers at 900 nanometers, providing a total focal shift range of about 10 micrometers. FIG. 17, with corresponding surface properties given in Table 9, shows a focal shift range from about negative 10 micrometers at 475 nanometers, to about three micrometers at around 725 nanometers, for a total focal shift range of 13 micrometers. This focal shift provided by the inventive optical relay system minimizes the variance of focal position as a function of wavelength which would ordinarily be present due to chromatic aberration of a conventional rod lens relay pair.

TABLE 8

Surface Data Summary for one implementation of the embodiment shown in FIG. 15

| Surface | Radius | Thickness | Index | Abbe no. | Clear Diam |
|---|---|---|---|---|---|
| Obj | Infinity | 6.0 | Air | | 4.2 |
| 1 | 23.0368 | 55.533 | 1.618 | 49.82 | 6.48 |
| 2 | Infinity | 2.5 | 1.497 | 81.55 | 6.48 |
| 3 | −6.6931 | 1.4 | 1.512 | 64.98 | 6.48 |
| 4 | −20.6228 | 0.25 | Air | | 6.48 |
| STO | Infinity | 0.25 | Air | | 5.7193 |
| 6 | 20.6228 | 1.4 | 1.512 | 64.98 | 6.48 |
| 7 | 6.6931 | 2.5 | 1.497 | 81.55 | 6.48 |
| 8 | Infinity | 55.533 | 1.618 | 49.82 | 6.48 |
| 9 | −23.0368 | 6.0 | Air | | 6.48 |
| IMA | Infinity | | | | 4.2557 |

TABLE 9

Surface Data Summary for one implementation of the embodiment shown in FIG. 15

| Surface | Radius | Thickness | Index | Abbe no. | Clear Diam |
|---|---|---|---|---|---|
| Obj | Infinity | 6.0 | Air | | 4.2 |
| 1 | 18.2447 | 42.835 | 1.620 | 36.37 | 6.48 |
| 2 | Infinity | 2.5 | 1.497 | 81.55 | 6.48 |
| 3 | −6.2847 | 1.4 | 1.525 | 64.67 | 6.48 |
| 4 | −16.6115 | 0.25 | Air | | 6.48 |
| STO | Infinity | 0.25 | Air | | 4.5273 |
| 6 | 16.6115 | 1.4 | 1.525 | 64.67 | 6.48 |
| 7 | 6.2847 | 2.5 | 1.497 | 81.55 | 6.48 |
| 8 | Infinity | 42.835 | 1.620 | 36.37 | 6.48 |

TABLE 9-continued

Surface Data Summary for one implementation of the embodiment shown in FIG. 15

| Surface | Radius | Thickness | Index | Abbe no. | Clear Diam |
|---|---|---|---|---|---|
| 9 | −18.2447 | 6.0 | Air | | 6.48 |
| IMA | Infinity | | | | 4.2720 |

Figure 18:
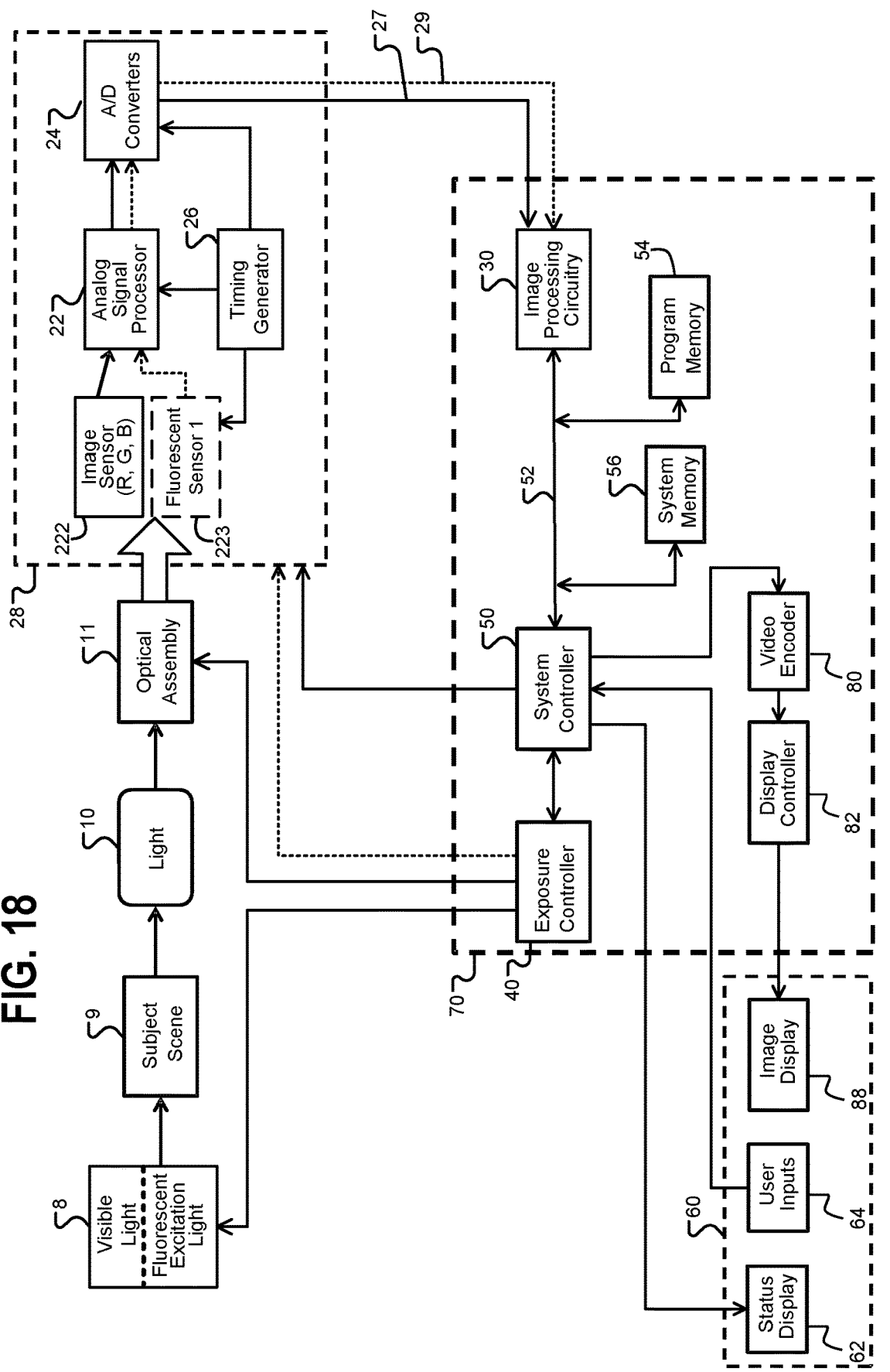
FIG. 18 is a hardware block diagram of system including an example image capture device according to an example embodiment of the invention.

Referring to FIG. 18, a block diagram of system including an image capture device and an endoscope device having an improved correction of chromatic aberration as described above. The invention is applicable to more than one type of device enabled for image capture, such as FI-capable endoscopes, other FI medical imaging devices. The preferred version is an imaging scope system, such as an endoscope.

As shown in the diagram of an endoscope device system, a light source 8 illuminates subject scene 9 with visible light and/or fluorescent excitation light, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is focused to form an image at a solid-state image sensor(s) 222 and/or fluoresced light sensor(s) 223.

Optical assembly 11 includes an optical relay system constructed according to the techniques provided herein. For example, the embodiments of FIG. 3, FIG. 5, FIG. 7, FIG. 9, FIG. 12, or FIG. 15 may be used, or other embodiments. An additional lens group may be included at the camera head, as discussed with respect to FIG. 2. As discussed above, portions of the optical assembly may be embodied in a camera head or other first optical device, while other portions are in an endoscope or other scope device, or the optical assembly 11 may be contained in a single imaging device. Image sensor 222 (which may include separate R, G, and B sensor arrays) and fluoresced light sensor 223 convert the incident visible and invisible light to an electrical signal by integrating charge for each picture element (pixel). It is noted that fluoresced light sensor 223 is shown as an optional dotted box because embodiments may use the RGB image sensor 222 to detect only white light images or to also detect fluoresced light (e.g., NIR, ICG, FI). The latter scheme may be used when the fluoresced light is in a spectrum detectable by image sensor 222 that is in or near the visible light spectrum typically detected by a RGB sensor arrays.

Of course, alternate implementations of the present inventive relay lens systems are possible. For example, optical assembly 11 may include a dichroic beam splitting element and may direct one band of the spectra to one sensor for visual imaging and another band to another sensor for fluorescence imaging. As the present invention enables a scope side solution to the problems associated with chromatic aberration in relay systems, the camera head image sensor assembly 28 need not be adjusted to assure both visible and FI images are in focus.

The image sensor 222 and fluoresced light sensor 223 may be active pixel complementary metal oxide semiconductor sensor (CMOS APS) or a charge-coupled device (CCD).

The total amount of light 10 reaching the image sensor 222 and/or fluoresced light sensor 223 is regulated by the light source 8 intensity, the optical assembly 11 aperture, and the time for which the image sensor 222 and fluoresced light sensor 223 integrates charge. An exposure controller 40 responds to the amount of light available in the scene given the intensity and spatial distribution of digitized signals corresponding to the intensity and spatial distribution of the light focused on image sensor 222 and fluoresced light sensor 223.

Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 222 and fluoresced light sensor 223 integrate charge. The control connection from exposure controller 40 to timing generator 26 is shown as a dotted line because the control is typically indirect.

Typically, exposure controller 40 has a different timing and exposure scheme for each of sensors 222 and 223. Due to the different types of sensed data, the exposure controller 40 may control the integration time of the sensors 222 and 223 by integrating sensor 222 up to the maximum allowed within a fixed 60 Hz or 50 Hz frame rate (standard frame rates for USA versus European video, respectively), while the fluoresced light sensor 223 may be controlled to vary its integration time from a small fraction of sensor 222 frame time to many multiples of sensor 222 frame time. The frame rate of sensor 222 will typically govern the synchronization process such that images frames based on sensor 223 are repeated or interpolated to synchronize in time with the 50 or 60 fps rate of sensor 222.

Analog signals from the image sensor 222 and fluoresced light sensor 223 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 222 also functions to detect the fluoresced light, fluoresced light data is included in the image signal 27, typically in one or more of the three color channels.

Image processing circuitry 30 includes circuitry performing digital image processing functions to process and filter the received images as is known in the art. Image processing circuitry may include separate, parallel pipelines for processing the visible light image data and the FI image data separately. Such circuitry is known in the art and will not be further described here.

Image processing circuitry 30 may provide algorithms, known in the art, for combining visible light imagery with FI imagery in a combined image display, and further highlighting or emphasizing the FI imagery for easily distinguishing the presence of fluorescing features in the image.

Timing generator 26 produces various clocking signals to select rows and pixels and synchronizes the operation of image sensor 222 and fluorescent sensor 223, analog signal processor 22, and A/D converter 24. Image sensor assembly 28 includes the image sensor 222 and fluorescent sensor 223, adjustment control 20, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between at least two modes, visible light and FI modes, and more preferably a combined mode is included in which FI images are combined or overlaid with visible images in a suitable manner known in the art. Such settings may include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control unit (CCU) 70.

CCU 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A relay system for an endoscope comprising:
an opposing pair of rod lens assemblies positioned symmetrically with respect to a central airspace, wherein each rod lens assembly includes optical elements consisting essentially of:
a meniscus lens positioned immediately adjacent to a central airspace and with the convex surface facing the airspace;
a first lens having positive power with a convex face positioned adjacent to the inner face of the meniscus lens, the first lens formed of a material having anomalous partial dispersion;
a rod lens, adjacent to the first lens having positive power, having a first face and a second face, both first and second faces being beam passing faces; and
an outer optical manipulating structure selected from the group consisting of:
(i) the second face of the rod lens, being concave, positioned adjacent to a second lens having positive power and having a convex face facing the second concave face of the rod lens;
(ii) the second convex face of the rod lens, being convex, positioned adjacent to an outer meniscus lens;
(iii) the second face of the rod lens, being plano, positioned adjacent to a second plano convex lens having a convex face facing the second plano face of the rod lens with a separation gap; and
(iv) the second face of the rod lens, being convex;
wherein the meniscus lens, the first lens having positive power, the rod lens, and the outer optical manipulating structure together provide chromatic aberration correction by manipulating light from the blue region of the spectrum through the near IR region of the spectrum to follow the same sequence of optical surfaces and come to a common focus in a common image plane.

2. The relay system of claim 1, wherein the first lens having positive power is plano-convex.

3. The relay system of claim 1, wherein the first lens having positive optical power is manufactured from a material having an Abbe number equal to or greater than 80.

4. The relay system of claim 1, wherein the outer optical manipulating structure is the second, concave face of the rod lens positioned adjacent to a second lens having positive power and having a convex face facing the second concave face of the rod lens.

5. The relay system of claim 4, wherein the second lens having positive power is plano-convex.

6. The relay system of claim 4, wherein each rod lens assembly has no additional optical manipulating elements other than the those listed.

7. The relay system of claim 1, wherein the outer optical manipulating structure is the second convex face of the rod lens positioned adjacent to an outer meniscus lens.

8. The relay system of claim 7, wherein each rod lens assembly has no additional optical manipulating elements other than the those listed.

9. The relay system of claim 1, wherein the outer optical manipulating structure is the second plano face of the rod lens positioned adjacent to a plano-convex lens having a convex face facing the second plano face of the rod lens with a separation gap.

10. The relay system of claim 9, wherein each rod lens assembly has no additional optical manipulating elements other than the those listed.

11. The relay system of claim 1, wherein the outer optical manipulating structure is the second convex face of the rod lens.

12. The relay system of claim 11, wherein each rod lens assembly has no additional optical manipulating elements other than the those listed.

13. The relay system of claim 1, wherein the relay system is also corrected for astigmatism.

14. The relay system of claim 1, wherein the meniscus lens is constructed of a crown glass having a refractive index less than 1.65 and an Abbe number between 55 and 75.

15. The relay system of claim 1, wherein the chromatic aberration correction is provided from approximately 400 nm to 900 nm.

16. The relay system of claim 1, wherein the pair of rod lens assemblies is arranged around an air space containing an aperture stop.

17. The relay system of claim 1, further comprising an endoscope containing the relay system.

18. The relay system of claim 1, wherein the first and second faces of the rod lens are plano.

* * * * *